United States Patent
Jones (10) Patent No.: US 11,049,617 B2
(45) Date of Patent: Jun. 29, 2021

(54) METHOD FOR TRANSFERRING OPERATIONAL DATA TO A MEDICAL DEVICE LOCATED WITHIN A HEALTHCARE ENVIRONMENT

(71) Applicant: Fresenius Vial SAS, Brezins (FR)

(72) Inventor: Alaster Jones, Saint Sauveur (FR)

(73) Assignee: Fresenius Vial SAS, Brézins (FR)

( * ) Notice: Subject to any disclaimer, the term of this patent is extended or adjusted under 35 U.S.C. 154(b) by 748 days.

(21) Appl. No.: 14/765,121

(22) PCT Filed: Feb. 24, 2014

(86) PCT No.: PCT/EP2014/053550
§ 371 (c)(1),
(2) Date: Jul. 31, 2015

(87) PCT Pub. No.: WO2014/131730
PCT Pub. Date: Sep. 4, 2014

(65) Prior Publication Data
US 2015/0370973 A1    Dec. 24, 2015

Related U.S. Application Data (60) Provisional application No. 61/769,948, filed on Feb. 27, 2013.

(30) Foreign Application Priority Data

Feb. 27, 2013    (EP) .................................... 13305223

(51) Int. Cl.
*G16H 40/40*    (2018.01)
*G16H 40/67*    (2018.01)
(Continued)

(52) U.S. Cl.
CPC ............. *G16H 70/40* (2018.01); *G16H 20/17* (2018.01); *G16H 40/40* (2018.01); *G16H 40/67* (2018.01)

(58) Field of Classification Search
USPC ........................................................ 705/2, 3
See application file for complete search history.

(56) References Cited

U.S. PATENT DOCUMENTS 6,327,535 B1 * 12/2001 Evans ....................... G01S 1/68
701/300
8,051,414 B2 * 11/2011 Stender .................. G16H 40/40
717/168
(Continued)

FOREIGN PATENT DOCUMENTS

| JP | 2007-140775 | 6/2007 |
| JP | 2007-526024 | 9/2007 |

(Continued)

OTHER PUBLICATIONS

Lor Siv-Lee, "Implementation of Wireless 'Intelligent' Pump IV Infusion Technology in a Not-for-Profit Academic Hospital Setting", Hospital Pharmacy vol. 42, No. 9, pp. 832-840 (Year: 2007).*
(Continued)

*Primary Examiner* — Joshua B Blanchette
(74) *Attorney, Agent, or Firm* — Cook Alex Ltd.

(57) ABSTRACT

A method for transferring operational data to a medical device (31, 32) for administering a drug to a patient, the medical device (31, 32) being located in a healthcare environment (3) and connected to a local network (33), comprises the steps of: transferring operational data to be transferred to the medical device (31, 32) to a communication device (40, 41); reading, by means of the communication device (40, 41), information from an identification tag (8) attached to the medical device (31, 32), wherein the information causes the communication device (40, 41) to
(Continued)

access a communication interface (310, 320, 340) associated with the medical device (31, 32); and transferring the operational data from the communication device (40, 41) via the communication interface (310, 320, 340) to the medical device (31, 32). By these means a method is provided which in an easy and comfortable, yet reliable way allows transferring operational data from an external server to a medical device located within a non-public, local network within a hospital environment.

16 Claims, 5 Drawing Sheets

(51) Int. Cl.
*G16H 70/40* (2018.01)
*G16H 20/17* (2018.01)

(56) References Cited

U.S. PATENT DOCUMENTS

| | | | |
|---|---|---|---|
| 9,135,393 B1* | 9/2015 | Blomquist | G06F 19/3468 |
| 2002/0083342 A1* | 6/2002 | Webb | H04L 67/2814 |
| | | | 726/12 |
| 2002/0169636 A1 | 11/2002 | Eggers et al. | |
| 2005/0108057 A1* | 5/2005 | Cohen | G16H 40/20 |
| | | | 705/3 |
| 2005/0137653 A1* | 6/2005 | Friedman | A61B 5/0002 |
| | | | 607/60 |
| 2007/0233521 A1* | 10/2007 | Wehba | G16H 40/67 |
| | | | 705/3 |
| 2008/0233925 A1 | 9/2008 | Sun et al. | |
| 2011/0264043 A1 | 10/2011 | Kotnik et al. | |
| 2013/0006666 A1* | 1/2013 | Schneider | G06F 19/326 |
| | | | 705/3 |
| 2013/0191513 A1* | 7/2013 | Kamen | G16H 40/67 |
| | | | 709/219 |
| 2013/0221084 A1* | 8/2013 | Doss | H04L 63/0492 |
| | | | 235/375 |

FOREIGN PATENT DOCUMENTS

| | | |
|---|---|---|
| JP | 2008-538708 | 11/2008 |
| JP | 2009-531146 | 9/2009 |
| JP | 2010-507176 | 3/2010 |
| JP | 2011-065481 | 3/2011 |
| WO | WO 03/094090 | 11/2003 |
| WO | WO2005/057466 A2 | 6/2005 |
| WO | WO2006/108304 A1 | 10/2006 |
| WO | WO2007/126948 | 11/2007 |
| WO | WO2008/057729 A2 | 5/2008 |
| WO | WO2012/054657 | 4/2012 |

OTHER PUBLICATIONS

Richard Swim, "Deployment of an Enterprise Wireless Infusion Pump Management System," IT Horizons, 2008, pp. 29-32 (Year: 2008).*

Lor Siv-Lee et al., "Implementation of Wireless "Intelligent" Pump IV Infusion Technology in a Not-for-Profit Academic Hospital Setting," Hospital Pharmacy vol. 42, No. 9, pp. 832-840 2007 Wolters Kluwer Health, Inc. (Year: 2007).*

Siv-Lee et al., "Implementation of Wireless 'Intelligent' Pump IV Infusion Technology in a Not-for-Profit Academic Hospital Setting", Hospital Pharmacy, vol. 42, No. 9, pp. 832-840 (Sep. 1, 2007).

International Search Report and Written Opinion, counterpart International Appl. No. PCT/EP2014/053550 (dated Oct. 14, 2014).

* cited by examiner

METHOD FOR TRANSFERRING OPERATIONAL DATA TO A MEDICAL DEVICE LOCATED WITHIN A HEALTHCARE ENVIRONMENT

The present application is a U.S. National Stage of PCT International Patent Application No. PCT/EP14/53550, filed Feb. 24, 2014, which claims the benefit of U.S. Provisional Appl. No. 61/769,948, filed Feb. 27, 2013, and priority to EP Application No. 13305223.3, also filed Feb. 27, 2013, all of which are hereby incorporated herein by reference.

The invention relates to a method for transferring operational data to a medical device for administering a drug to a patient, the medical device being located in a healthcare environment and connected to a local network.

Operational data in this context may be drug library data or other data such as configuration data relating to the operation of a medical device such as an infusion pump.

Typically, medical devices for administering a drug to a patient, such as infusion pumps, are installed at various locations in a healthcare environment, for example in a hospital. Such medical devices may for example be located in different rooms of wards of a hospital or in operating rooms. Nowadays, such medical devices are connected to a local network for communicating via wired or wireless means with a hospital management system hosted on a server located in the healthcare environment. For example, a group of infusion pumps may be installed on a rack serving as a communication link to the local network such that via the rack the infusion pumps are connected to the local network and are operative to communicate with a hospital management system on a server within the healthcare environment, for example within a hospital, via the local network, for example a local area network (LAN) or a wireless local area network (WLAN). Or a single pump may have a wireless or wired communication connection to the local network and a hospital information system.

To control the operation of medical devices of this kind for administering drugs to a patient, so called drug libraries are installed on such medical devices, a drug library comprising drug library data characterizing a drug, its ingredients, rules for compatibility and rules for administration or the like. A drug library may for example comprise a list of drugs in which each drug is associated with parameters defining for example boundary values for administration by means of an infusion device. Such boundary values may for example relate to a minimum and maximum dosage for administering a particular drug, a minimum and maximum rate for administering a drug, a minimum and maximum time of administration and the like. In addition, such boundary values may be dependent on the age, weight and gender of a patient and, hence, may be patient-specific.

By using such drug libraries the operation of a medical device such as an infusion pump for administering a particular drug to a patient is controlled in that the medical device may be operated by a nurse only within the boundaries posed by the drug library. For this, for administering a drug to a patient, the nurse identifies the drug to the medical device, upon which the medical device automatically loads the respective rules and boundary values from a drug library installed on the medical device.

Presently, such drug libraries are locally installed within a healthcare environment, for example within a hospital (or group of hospitals). Such drug libraries are for example installed as software on a personal computer (PC) or a server within a hospital, from which the drug library may be distributed to medical devices located in different wards of a hospital in order to be installed on such medical devices.

With systems presently in use it is cumbersome to distribute drug library software within a healthcare environment and, in particular, to keep drug library software up to date throughout the entire healthcare environment. This may lead to multiple variants of drug libraries being used within a healthcare environment, for example within a particular hospital, posing a risk for safety due to the possibility of multiple references of drug libraries with possibly inconsistent data.

There is a desire to provide operational data to medical devices such as infusion pumps for administering a drug to a patient or a rack for holding multiple infusion pumps from an externally hosted ("cloud" or "web-based") server. Such an external server, however, is located outside of the healthcare environment and hence outside of the local network, such that communication with medical devices located within the healthcare environment is not always possible because the local network of the healthcare environment is logically separated from external communication networks such as the internet.

Hence, to be able to provide data from an external server to medical devices located within the healthcare environment, there is a need for means to securely and reliably transfer data to the medical devices.

WO 2012/054657 A2 discloses a method for performing mobile medical information management. A web-based patient portal is accessed and medical history records of a patient are downloaded therefrom, based upon a user profile including personal information that uniquely identifies the patient. The download data can be output to a patient or a physician treating the patient.

Within a method known from WO 2007/126948 A2 a medication management unit associated with a medical device performs a medication order for administering a drug to a patient. The medication management unit identifies the medical device such as an infusion pump by means of its network IP address and monitors the general physical location of the medical device. A medication order is transmitted to the medication management unit, which then performs the medication order.

It is an object of the invention to provide a method which in an easy and comfortable, yet reliable way allows transferring operational data from an external server to a medical device located within a non-public, local network within a hospital environment, for example a small hospital with limited IT infrastructure.

This object is achieved by a method comprising the features of claim 1.

Accordingly, a method for transferring operational data to a medical device for administering a drug to a patient comprises the steps of:

transferring operational data to be transferred to the medical device to a communication device, reading, by means of the communication device, information from an identification tag attached to or displayed on the medical device, wherein the information causes the communication device to access a communication interface associated with the medical device, and transferring the operational data from the communication device via the communication interface to the medical device.

The instant invention is based on the idea to transfer data to a medical device via a communication device such as a portable device in the shape of a personal digital assistant (PDA), a smart phone, a tablet computer, a laptop computer or the like. The communication device comprises a reading device for reading a physical identification tag attached to or displayed on the medical device such as a barcode, an RFID tag or another identification tag capable of carrying machine-readable information, the identification tag containing information for identifying the medical device and for causing the communication device to connect with a communication interface such as a web server associated with the medical device. The identification tag read by the communication device hence serves to direct the communication device to the communication interface such as a web server, and via the communication interface the operational data is transferred from the communication device to the medical device.

The communication interface hence serves as a communication link to allow for a transfer of operational data such as drug library data from the communication device to the medical device. The communication device may furthermore be constituted to provide operational information about the medical device such that a user may, via the communication device, access for example a monitoring page provided by the communication interface which provides information about the operation of the medical device. For example, via the communication interface information about a current infusion operation of an infusion pump, such as an infusion rate, an infusion time and an infusion dosage or the like, may be output to the communication device such that a user via the communication device may monitor an infusion operation.

The communication interface may also be constituted to allow for an input of command data such that a user may enter a command relating for example to an infusion operation and hence may control a medical device such as an infusion device via the communication device connected to the communication interface.

By means of the proposed method, data are transferred to a medical device located within a non-public, local network in a healthcare environment. For this, the communication device is directed by means of the identification tag to the communication interface and via the communication interface communicates with the medical device to transfer the data to the medical device. The communication interface in the shape of a web server herein may be implemented on an infusion device for administering a drug to a patient, on a rack constituted to be connected to one or multiple infusion pumps or on a distribution server (for example in the shape of a centralising gateway) located in the healthcare environment and connected to the local network.

If the communication interface such as a web server is implemented on the infusion pump, it is a part of the infusion pump and allows for a direct transfer of data from the communication device to the infusion pump. If the communication interface is installed on a rack, the data is transferred from the communication device to the rack and is then distributed from the rack to one or multiple infusion pumps connected to the rack such that the rack serves for distributing the data to the single infusion pumps. If the communication interface is located on a separate distribution server, the communication device transfers the data to the distribution server, and from the distribution server the data is then distributed to one or multiple medical devices such as infusion pumps and/or racks located in the healthcare environment.

As said, the communication interface beneficially is constituted by a web server. The information obtained from the identification tag corresponds to the IP address/hostname or other unique identifier that allow it to direct to a HTTP address of a web page on the web server such that by reading out the information from the identification tag the communication device is directed to the web server. The communication device hence opens a web link and automatically or after a user confirmation connects to the web server.

A web server in this regard is understood as a device implemented by software or hardware which serves to deliver web content to a communication device accessing the web server. The web server for example holds a website and hence is constituted to deliver web pages on request to a client using the so-called hypertext transfer protocol (HTTP). This includes the delivery of HTML documents and any additional content that may be included in a document.

The identification tag may, as said, for example, be a barcode or an RFID tag. The identification tag contains information which directs the communication device to the communication interface. The identification tag may have encoded for example the IP address or HTTP address of a web server.

The identification tag, in particular the barcode, may be static or dynamic. A static identification tag herein is to be understood as non-changeable. A static barcode may be physically attached to a medical device and for example may be a sticker or the like. A static identification tag, for example a barcode, may also be displayed on a display of the medical device. A dynamic identification tag, for example a barcode, is changeable in its contents and information it contains. A dynamic identification tag hence may be dynamically adapted. Such dynamic identification tag may for example be displayed on a display of the medical device in a non-static fashion.

If the identification tag is a barcode, the communication device comprises a suitable barcode reading device. If the identification tag is an RFID tag, the communication device comprises a suitable RFID reading device.

The communication device may be constituted by a personal computer (PC), a notebook computer, a personal digital assistant (PDA), a mobile phone or any other device allowing for a connection to the internet. Preferably it is constituted by a portable device.

In the context of this text a drug library is to be understood as a list of drugs in which each of the drugs is associated with parameters defining operational boundaries for administering the particular drug to a patient. Such parameters may depend on the patient demographics, for example the patient's age, weight or gender.

Furthermore, in the context of this text a local network shall be understood as a non-public communication network (also referred to as intranet), in this regard being distinguished from a public communication network such as the internet.

A healthcare environment may be for example a healthcare institution such as a hospital. A hospital typically has a certain number of wards each having multiple patient bedrooms. A healthcare environment may, however, also be a group of several hospitals belonging to a single healthcare group, for example being run by a single hospital carrier using a common local network (intranet).

Within the healthcare environment different medical devices for administering drugs to patients may be present. The medical device may for example be an infusion pump such as a syringe pump or a volumetric pump. The medical devices may origin from a single manufacturer or from different manufacturers.

The medical device may also be constituted as a rack to which one or multiple infusion pumps can be connected. The rack in this case serves as a communication link for carrying the infusion pumps and for connecting them to the local network for communication with a hospital management system of the healthcare environment. In this case, both the rack and the infusion pumps form medical devices to which operational data may be installed (drug library data may for example be installed on a rack for distribution to infusion pumps connected to the rack).

In one embodiment the operational data is transferred to the communication device from a drug library server located within a public communication network. This is based on the idea to provide a web-based service for providing operational data. Operational data herein is contained and stored on a drug library server located within a public communication network such as the internet. By means of a web based service it becomes possible to allow users to create drug libraries online and to easily share operational data between medical devices within a particular healthcare environment and across different healthcare environments. It furthermore becomes possible to create, share and map external information such as information from external data bases such as the U.S. National Library of Medicine to medical devices. By means of such a web based service drug libraries within a healthcare environment and across several healthcare environments can easily be managed, allowing for an easy distribution and updating of operational data.

Such a system allows for an easy creation, editing and sharing of drug libraries by providing a web based service. The communication device may comprise a web client for communicating with the drug library server via the public communication network, for example via the internet. Via the communication device, hence, a user may connect to the drug library server to create a drug library, edit drug library data and manage the sharing of a created drug library.

By accessing the drug library server over the public communication network, for example the internet, a user may manage drug libraries to be used in a healthcare environment and manage its distribution and sharing properties. A user herein may via the internet be allowed to edit his personal settings, to edit collaboration settings to allow for a sharing of operational data such as drug library data between different users, services, wards or hospitals, to define the distribution of drug libraries within a particular hospital by defining care areas relating to subareas such as wards of a hospital or to create a complete data set mapping the entire drug library structure of a hospital or even a group of hospitals. In addition to drug library data the user herein can also set configuration data relating to medical devices such as infusion pumps, such configuration data being contained in a so called configuration and setting operational rules for a medical device for example to customize a display area of the medical device or to define parameters of particular security features.

The drug library server is located within the public communication network and hence in the public domain, for example in the internet domain. The medical devices, in contrast, are located in the local network and hence in a non-public, private domain confined to the particular healthcare environment. The drug library server (in the public domain) hence is not able to freely communicate with the medical devices located within the non-public environment of the local network and hence cannot as such easily obtain information for example regarding the localization of medical devices within a particular healthcare environment. For transferring drug library data and also other, for example configuration data to the medical devices, the drug library server hence transfers the data to the communication device such as a mobile device in the shape of a PDA or a laptop computer, and via the communication device the data is transferred to the medical device. The drug library server can communicate with the communication device via the public communication network such as the internet and may alert the communication device once a newly published set of data for a particular medical device such as an infusion pump is available. A user may then download the data set to the communication device and may access the communication interface associated with the medical device by reading the identification tag attached to or displayed on the medical device to transfer, via the communication interface, the data to the medical device.

The drug library server advantageously exports its operational data in a common XML or JSON/BSON format (XML: Extensible Mark-up Language; JSON: Java Script Object Notation; BSON: Binary JSON). By outputting operational data in a commonly known and accepted format a drug library server of this kind may be used in connection with medical devices of different manufacturers by providing an output which is readable independent on the specific preferences and settings of a certain manufacturer installation.

The drug library server may however also output the operational data in another, possibly proprietary binary format.

The drug library server may also export the operational data in a so-called flat file format. A flat file can for example be a plain text file, usually containing one record per line, or a binary file. Within a record of a flat file, single fields can be separated by delimiters such as comma or tab characters, or may have a fixed length.

Or the drug library server, for transferring operational data to the communication device, may simply export a (partial) copy of a database which is stored on the drug library server such that the communication device receives a dataset in the shape of the (partial) copy of the entire database in a database format.

The idea underlying the invention shall subsequently be described in more detail with reference to the embodiments shown in the figures. Herein.

Figure 1:
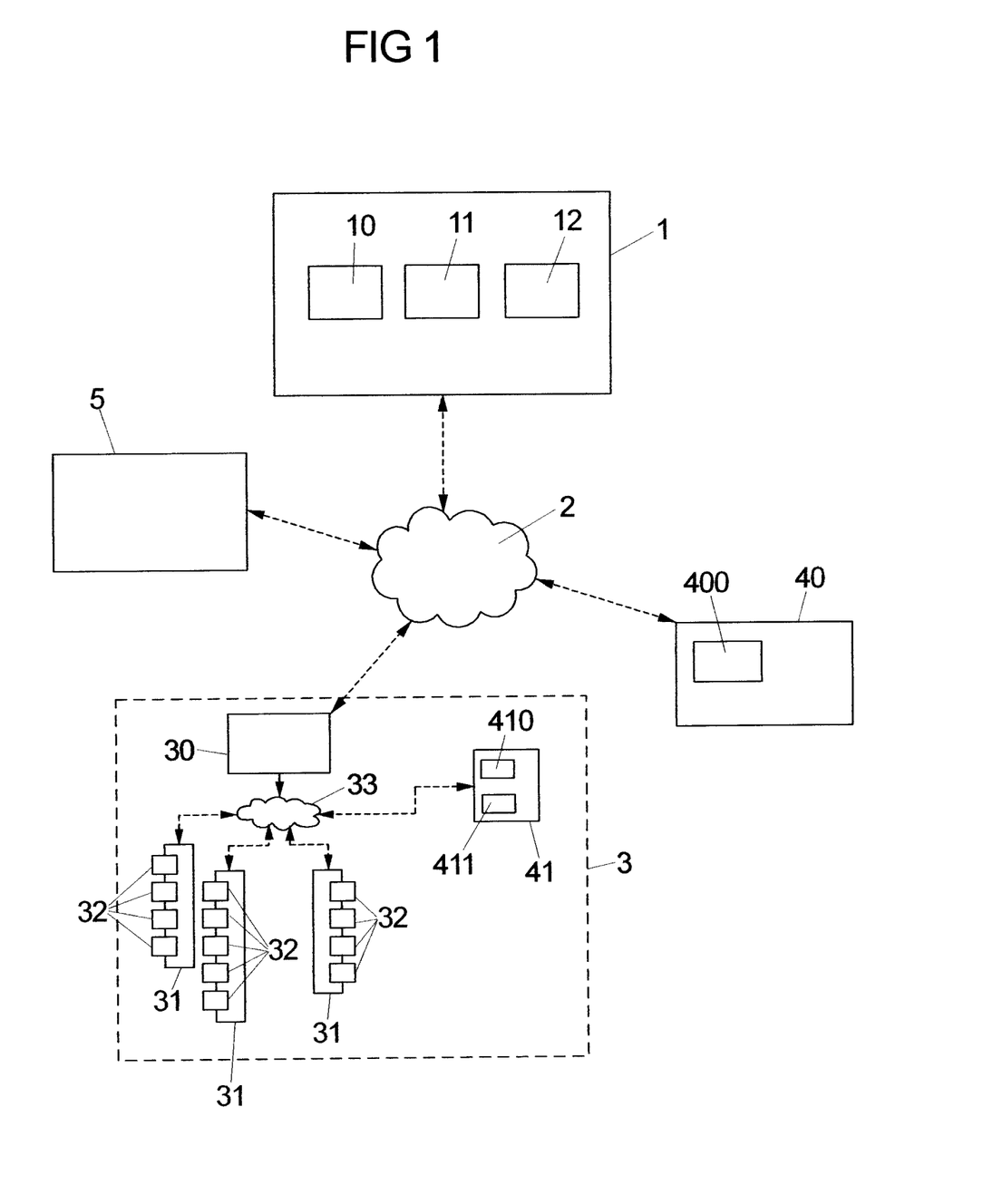
FIG. 1 shows a schematic overview of a system for providing operational data to a medical device.

FIG. 1 shows a schematic overview of a system for providing operational data to medical devices 31, 32, located within a healthcare environment 3.

A healthcare environment 3 in this regard may be for example a hospital. The hospital may be organized to have different clinics, departments, wards and operation facilities and the like. Throughout the hospital, a number of medical devices 31, 32 may be distributed serving to administer drugs to patients. Such medical devices may be infusion pumps 32 connected to racks 31, wherein the racks 31 serve as mechanical carriers for the infusion pumps 32 on the one hand and as communication links to facilitate communication between the infusion pumps 32 and a hospital local network 33 on the other hand. Via the racks 31 and the local network 33 (for example set up as a local area network (LAN)) the infusion pumps 32 may be connected to a hospital management system, hence, allowing for a centralized management of the infusion pumps 32 within the hospital local network 33.

The system as depicted in FIG. 1 provides a web-based service for providing operational data such as drug library data to medical devices 31, 32. Drug libraries, as they are conventionally known, serve to provide rules to medical devices 31, 32 for administering drugs to a patient. In particular, drug libraries in the context of infusion devices 32 contain a list of drugs in which each drug is associated with parameters that define, characterize and impose boundary values on an infusion device 32 for administering the particular drug to a patient. For example, such boundary values may relate to the dosage, the rate of administration and the time of administration for a drug and may vary for different drugs and also for different types of patients, for example dependent on the age, weight and gender of a patient.

The drug libraries are installed on the medical devices 31, 32, in particular on the infusion pumps 32, such that during operation of an infusion pump 32 parameters set by the drug library for a certain drug are applied. For example, a nurse is not enabled to choose a dosage rate outside a range of dosage rates defined by the applied drug library for a certain drug. If a certain drug is to be administered to a patient, a nurse can choose administration parameters only within the boundaries defined by the drug library.

In some conventional scenarios drug libraries are locally installed on a computer within the healthcare environment 3, for example, within a hospital management system and are distributed locally to the medical devices 31, 32. This makes it cumbersome to distribute new or updated drug libraries throughout an entire healthcare environment 3 without having duplicate variants of drug libraries being installed on different medical devices 31, 32.

By providing a web-based service for providing operational data, this problem is overcome in that a drug library server 1 is provided within a public domain. The drug library server 1 can be connected via a public communication network 2, for example the internet, to a communication interface 30, for example a router, within the healthcare environment 3 or can be connected directly to a local communication network 33. In case of connection to a public communication network 2, the drug library server 1 can interact with medical devices 31, 32 or a distribution server 34 trough hospital network equipment (for example the communication interface 30 such as a router within the healthcare environment 3). In case of direct connection to a local network 33, the drug library server 1 can directly interact with medical devices 31, 32 or the distribution server 34. In both cases, the drug library server 1 can interact with external services 5 through the public communication network 2. The drug library server 1 hosts a web server 10, communication interface components (web interface components) 11 and data based components 10.

Via the web server 10, the drug library server 1 provides data to web clients 400, 410 on communication devices 40, 41, constituted for example as portable devices, such as PDAs or portable computers or other smart devices, possibly with integrated camera or barcode scanners and/or NFC (Near field communication) features.

The web interface components 11 provide interfaces for interaction with an (internal or external) distribution server 34 and/or directly to the medical devices 31, 32 by means of, for example, the Hypertext Transfer Protocol (HTTP).

The database components 12 provide databases containing drug library data and other data relating to medical devices 31, 32 to be provided within the web-based service.

The web-based service provided by means of the drug library server 1 shall serve to support medical devices 31, 32, in particular infusion devices, of a particular manufacturer or universally for different manufacturers. The drug library server 1 herein shall run database components 12 combining the product knowledge and evolutions, client management and accounts, product services and sales. The drug library server 1 shall allow for a creation, uploading, downloading and/or managing of drug libraries online within a managed client space, wherein a client space may relate to a hospital group (several hospitals), an entire hospital, a particular service or to an individual user. The web-based service allows for an import or export of drug libraries to arbitrary communication devices 40, 41 such as mobile devices, smart devices, PCs or laptop computers or the like which can access the drug library server 1 via web clients 400, 411. The drug library server 1 furthermore may contain specific tools available for download, such tools facilitating the managing of medical devices 31, 32.

By means of the web-based service a service centred architecture is provided. The service allows for an easy upgrade and evolution of software components. The drug library server 1 holds client accounts, contacts, status reporting and management centrally. This alleviates an installation in a local healthcare environment domain such as a hospital. The centralized service also allows for a centralized product control and licensing and also allows, for the service operator, to perform a targeted marketing, to obtain usage statistics and to provide targeted usage services. By means of the drug library server 1 drug libraries can be easily created and shared online in a standardized way, wherein templates may be available for the creation of a drug library. By means of the web-based service the distribution and upgrading to keep drug libraries within a particular healthcare environment 3 and even across several healthcare environments 3 up to date is greatly facilitated.

Figure 2:
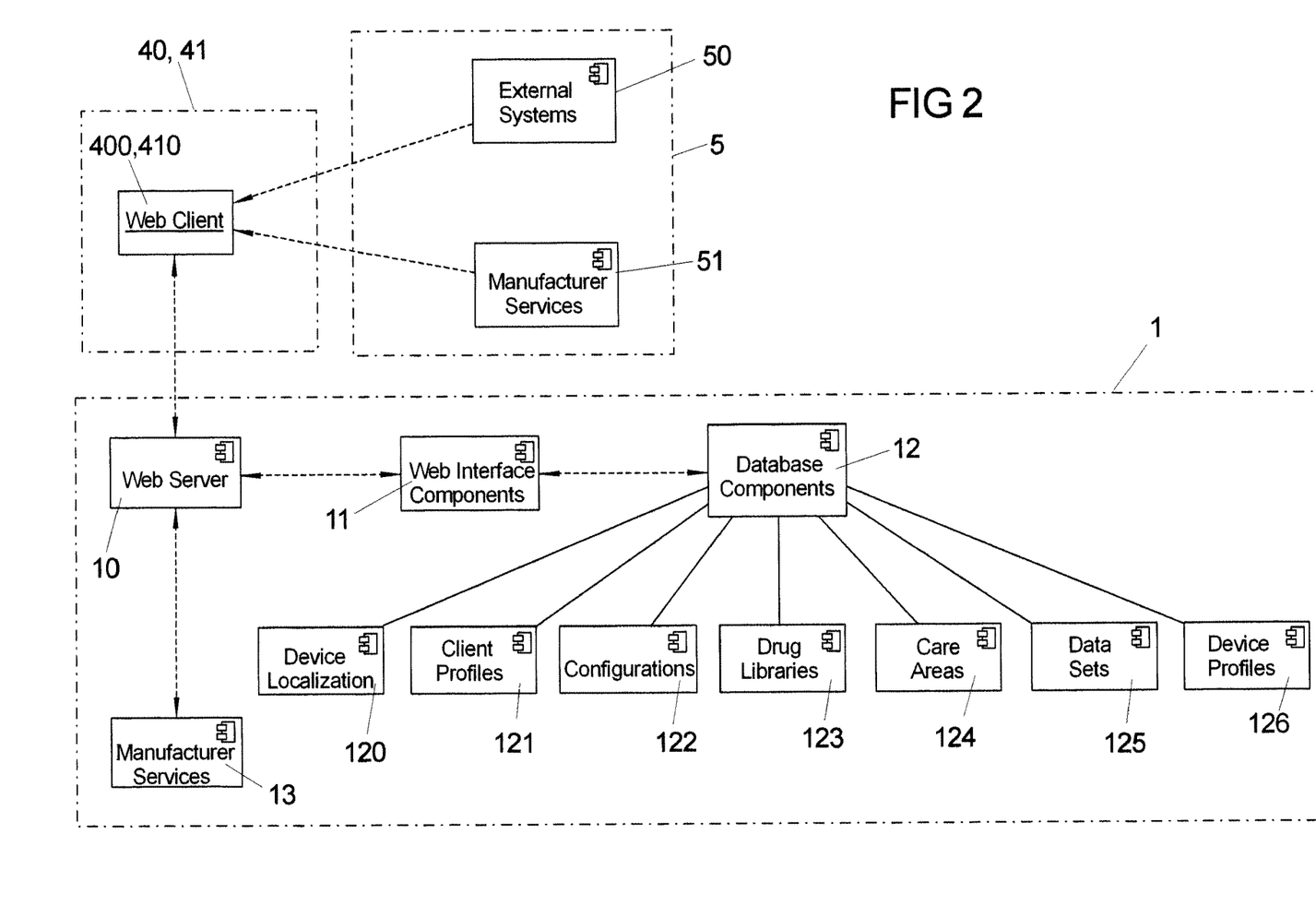
FIG. 2 shows a schematic overview of a drug library server of the system.

FIG. 2 shows a schematic overview of the drug library server 1. As already noted, the drug library server 1 holds a web server 10, web interface components 11 and database components 12. Via the web server 10 the drug library server 1 communicates with web clients 400, 410 of communication devices 40, 41, for example arbitrary mobile devices having a connection to the public communication network 2, for example the internet. Via the web server 10 a user can access the web interface components 11 and database components 12.

The database components 12 comprise various databases containing data with regard to the localization of a medical device (device localization 120), client profiles 121, configurations 122, drug libraries 123, care areas 124, data sets 125 and device profiles 126.

In addition, the drug library server 1 may contain manufacturer tools 13 provided for download to communication devices 40, 41. Among such tools may for example be a device discovery tool facilitating the localization of medical devices 31, 32 within a healthcare environment 3.

The web-based service may also interact and make use of external services 5 such as services provided by external systems 50 (external to a particular device manufacturer) or services of a particular device manufacturer (manufacturer services 51). By means of the external services 5 a user may map external information (for example from other data bases such as the U.S. National Library of Medicine) to medical devices 31, 32. External services 50 as U.S. National Library of Medicine can be used by the drug library server 1 or by the internal distribution server 34 to automatically or manually import data and transform the data to a dataset which is distributable and understandable by medical devices 31, 32. Manufacturer services 51 can be used by the drug library server 1 or by the internal distribution server 34 to automatically or manually import a dataset which is distributable and understandable by medical devices 31, 32. In both case, a user can interact with the drug library server 1 or with the internal distribution server 34 to import, modify and export datasets.

Within the web-based service the library server 1 is located outside the healthcare environment 3 within the domain of the public communication network 2 such as the internet. In contrast, the medical devices 31, 32 in the shape of infusion pumps and racks are placed inside the healthcare environment 3 in the domain of the non-public, local network 33 of the healthcare environment 3. Hence, a data transfer from the drug library server 1 to the medical devices 31, 32 to distribute newly published data sets in relation to drug library data requires means to deliver the data from outside the healthcare environment 3 to the medical devices 31, 32 located within the healthcare environment 3.

For this, the communication devices 40, 41—preferably shaped as portable devices such as smart phones, personal digital assistants (PDAs), tablet computers or laptop computers—are used to transport the data from the drug library server 1 to the medical devices 31, 32. Drug library data such as a newly published data set to be distributed to medical devices 31, 32 located in the healthcare environment 3 is in a first step downloaded to a communication device 40, 41, wherein the communication connection between the drug library server 1 and the communication device 40, 41 is set up via the public communication network 2 such as the internet. Once the data are downloaded to the communication device 40, 41, the data can be transferred to one or multiple medical devices 31, 32 if the communication device 40, 41 is placed within the healthcare environment 3 and is connected to the local network 33 of the healthcare environment 3.

For transferring the data from the communication device 40, 41 to a particular medical device 31, 32, an identification tag such as a barcode or an RFID tag, physically attached to the medical device 31, 32 in question or displayed on the medical device by means of a screen, is read by the communication device 40, 41. For this, the communication device 40, 41 comprises an appropriate reading device such as a barcode scanner or a RFID reading device. Upon reading the information contained in the identification tag, the communication device 40, 41 is directed to a communication interface associated with the medical device 31, 32 in question, and via the communication interface, which may be constituted by a web server, the data is transferred to the medical device 31, 32.

Figure 3:
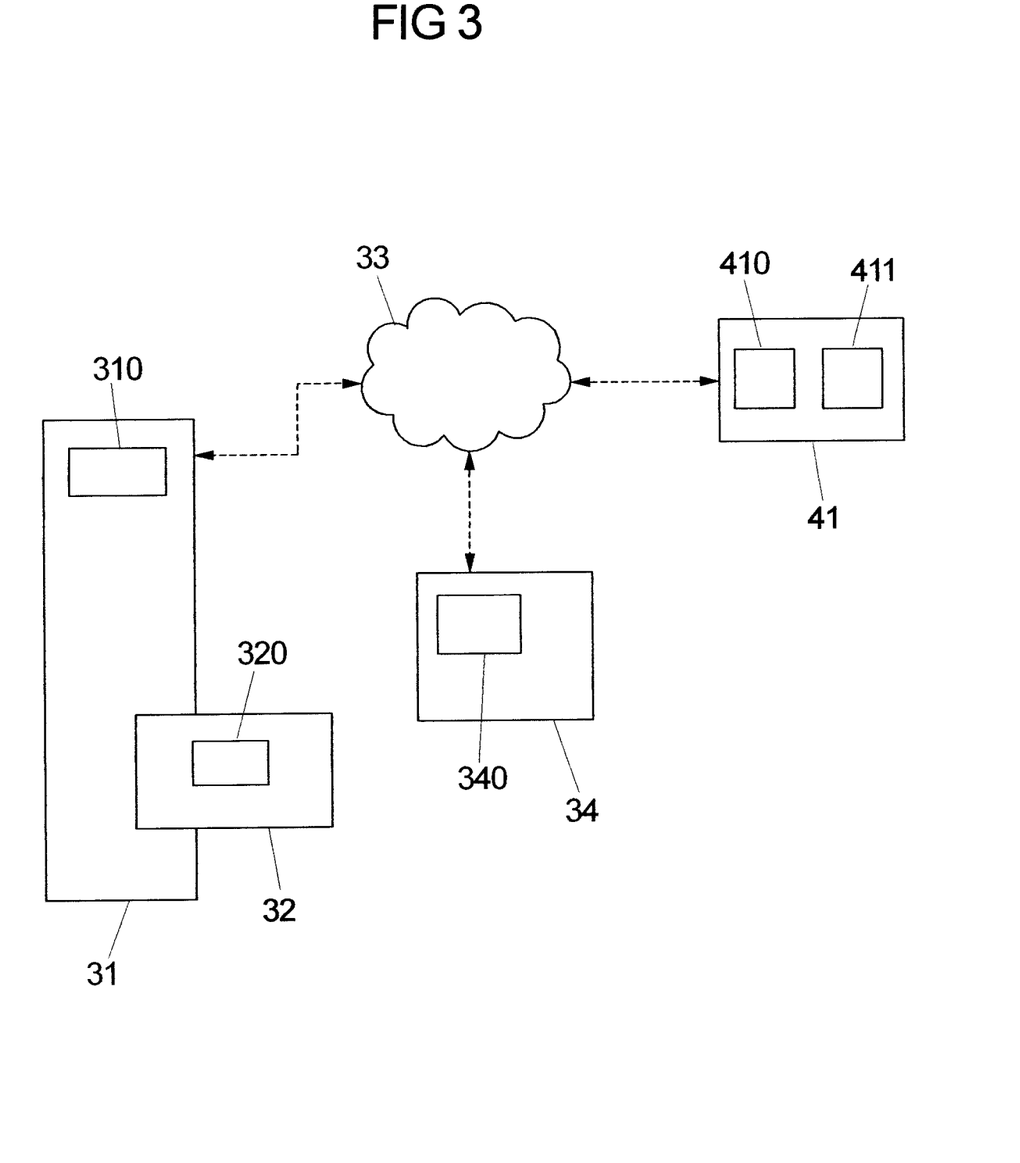
FIG. 3 shows a schematic view of devices arranged in a healthcare environment.

Different use cases arise and shall subsequently be described referring to FIG. 3, wherein possibly also other use cases are conceivable.

In a first use case the communication device 41, after having downloaded the data from the drug library server 1, scans a barcode attached to or displayed on, for example, an infusion device 32 attached to a rack 31. The infusion device 32 herein is connected via the rack 31 to the local network 33, and also the communication device 41 is connected to the local network 33 such that the communication device 41 and the infusion device 32 have access to the same communication network.

Upon scanning the barcode and reading out the information contained in the barcode, the communication device 41—automatically or involving a user interaction such as a confirmation—is directed to a communication interface 320 in the shape of a web server embedded in the infusion device 32. The information contained in the barcode typically may be the IP or hostname address or HTTP address of a page on the web server 320. The communication device 41 now opens the web link using the information obtained from the barcode, hence accessing the web page provided by the web server 320 and containing a file upload object. Automatically or by user interaction, the file to upload is now selected, wherein the file corresponds to a data set containing operational data such as drug library data which has been downloaded from the drug library server 1 to the communication device 41. The file is then transferred to the medical device 32, wherein the web server 320 may contain a backend which handles the received file for installation on the infusion device 32 and for a check of integrity, validity and persistency of the data contained therein.

In a second use case the communication device 41 is directed to—instead of a web server 320 embedded in the infusion device 32—a communication interface 310 in the shape of a web server of the rack 31. Upon direction to the web server 310 of the rack 31, the data is transferred to the rack 31, wherein the rack 31 distributes the data to infusion devices 32 attached to the rack 31.

A reference copy of the data herein may be stored on the rack 31 such that a data transfer may also take place for future device connections, i.e. if an infusion device 32 in the future is attached to the rack 31. In this regard, an infusion device 32 can be plugged to the rack 31, upon which the rack 31 validates the configuration of the attached infusion device 32 against its reference copy. If an update of the data installed on the infusion device 32 is necessary, the infusion device 32 may enter an update sequence with rack 31.

Other than that the second use case works just as the first use case described previously.

In a third use case, the communication device 41 may be directed to a distribution server 34 also connected to the local network 33 and placed within the healthcare environment 3. The distribution server 34 comprises a communication interface 340 in the shape of a web server, wherein the communication device 41 is directed to the web server 340 upon reading out the information contained in the barcode attached to or displayed on an infusion device 32 or a rack 31. The barcode hence is attached to or displayed on the infusion device 32 or the rack 31, but the web link information contained in the barcode directs the communication device 41 to the distribution server 34 and its web server 340. The data then is transferred to the distribution server 34, and the distribution server 34 takes care of distributing the data to the infusion device 32 and/or the rack 31.

For transferring the data for example to an infusion device 32, the infusion device 32 must be connected via the local network 33 to the distribution server 34 (otherwise an alert may indicate that the infusion device 32 is not connected to the local network 33). The transfer of a data set from the distribution server 34 to the infusion device 32 may then automatically or manually be invoked.

The above use cases relate to the transfer of data from the drug library server 1 via the communication device 40, 41 to the medical devices 31, 32. Rather than transferring data, other use cases involving the communication device 41 are conceivable.

For example, upon scanning a barcode attached to or displayed on a medical device such as an infusion device 32, the communication device 40, 41 may be directed to a supervision page provided by the embedded web server 320 of the infusion device 32. Via the supervision page, the communication device 41 may receive status information about the operation of the infusion device 32 such that, for example, a pumping operation may be monitored and information about an actual dosage rate, infusion time, administered drug or the like may be read out via the communication device 41.

A supervision page may also be provided by the web server 310 embedded in the rack 31 and containing supervision data about all infusion devices 32 connected to the rack 31. Or a supervision page may be provided by the web server 340 of the distribution server 34 providing information about racks 31 and infusion devices 32 connected to racks 31. In this regard, the communication device 41, upon reading information contained in a barcode attached to or displayed on an infusion device 32 or a rack 31, may be directed to the web server 310, 340 installed on the rack 31 or the distribution server 34.

In another use case, the communication device 41 may also be allowed to enter commands regarding the infusion operation of an infusion device 31 upon scanning a barcode attached to or displayed on the infusion device 32 and upon being directed to a respective command page provided by the web server 310, 320, 340 installed on the infusion device 32, the rack 31 or a distribution server 34. For example, via such a command page a user may set via the communication device 41 a stop alarm, may set a patient's name or may enter or amend other configuration data.

Figure 4:
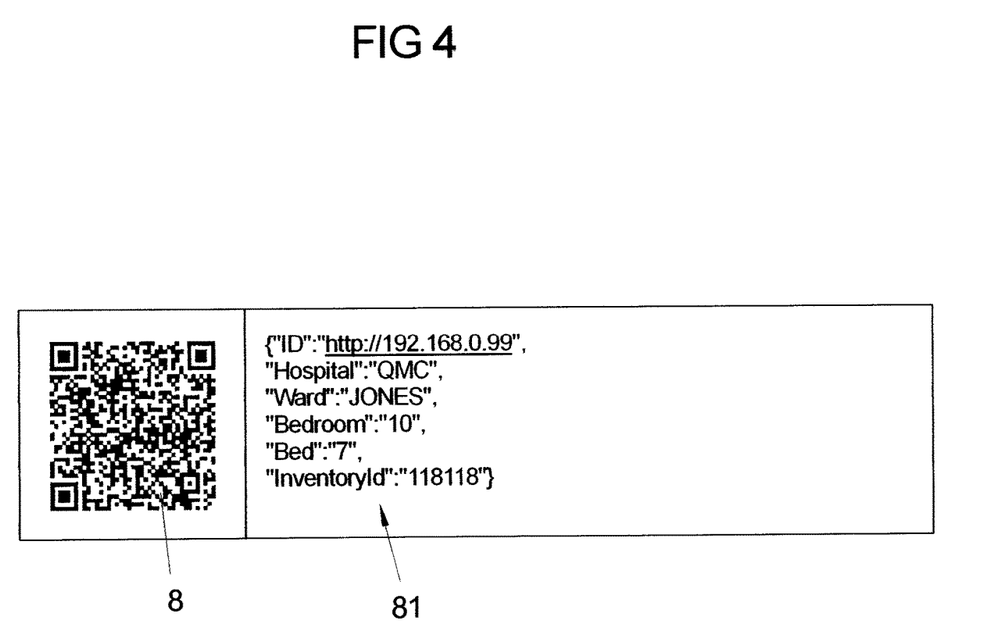
FIG. 4 shows an example of a barcode.

An example of a barcode 8 is shown in FIG. 4. The barcode 8 in this particular example encodes the data shown to the right including a unique identifier in the shape of a static IP address, a hospital name, a ward name, a bedroom number, a bed number and an inventory ID. A scan of the barcode 8 by means of a communication device 40, 41 such as a portable device (for example a mobile phone, a PDA, a tablet PC or the like) leads to a displaying of the information contained in the barcode 8 on the display of the communication device 40, 41.

A barcode 8 can also be displayed directly on a screen of a medical device 31, 32. In this case the barcode 8 may be static or dynamic. In case of a static barcode, the barcode values are set by a specific tool in a medical device 31, 32 in accordance with a device manager. In case of a static barcode, the device manager stores information using a unique identifier identifying the medical device 31, 32 (for example serial number or MAC Address) and the related barcode. In case of a dynamic barcode, the barcode 8 may be generated directly by the medical device 31, 32 (for example by using a unique identifier and timestamp, or by means of a random generator) or by the distribution server 34. In the latter case the distribution server 34 is responsible of keeping track of the unique identifier of a medical device 31, 32 in an associated barcode 8.

The IP address contained in the barcode 8 directs the communication 40, 41 to a web server 310, 320, 340 installed on the infusion device 32, the rack 31 or the distribution server 34. The web link herein is established automatically or by tapping on the display of the communication device 40, 41 (if the communication device 40, 41 comprises a touch screen), provided the communication device 40, 41 is on the hospital local network 33.

Figure 5:
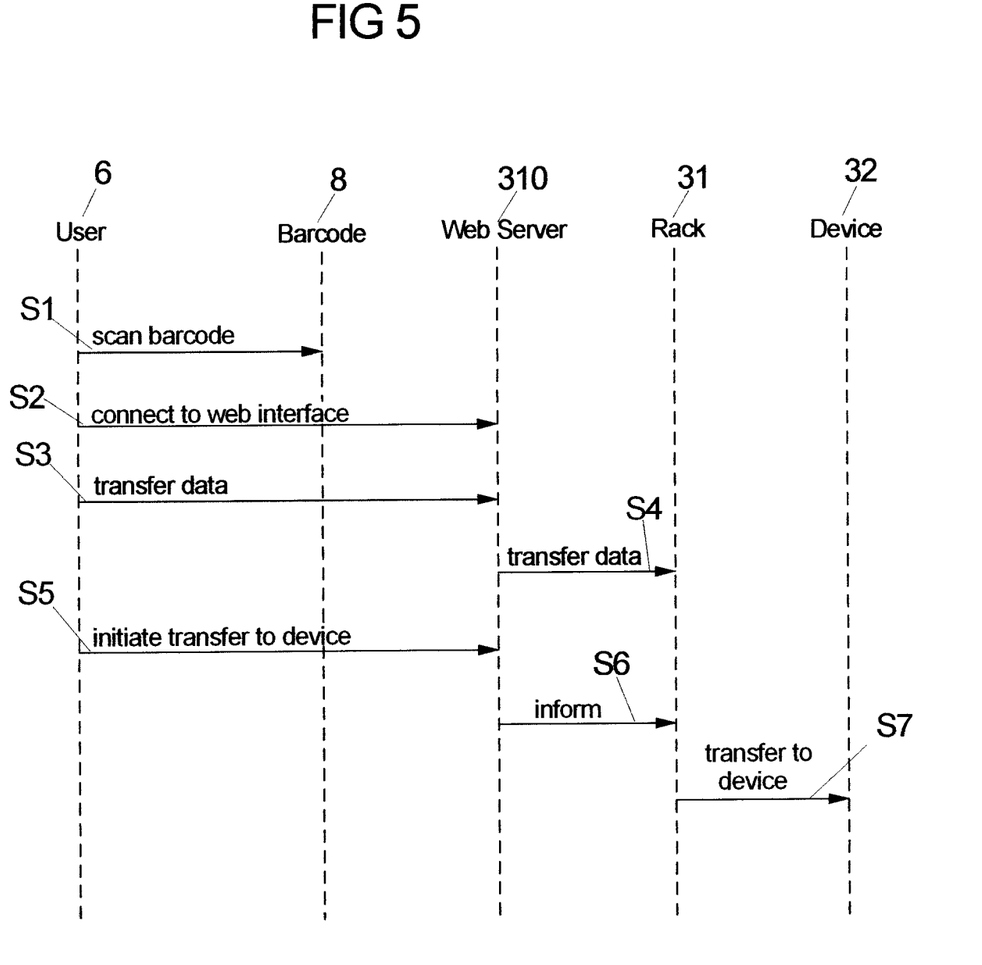
FIG. 5 shows a schematic sequence diagram for transferring operational data to a medical device.

In FIG. 5 a sequence diagram for transferring operational data via the web server 310 of a rack 31 to an infusion device 32 attached to the rack 31 is shown. In a first step, a certain drug library dataset is downloaded by a user 6 to a communication device 40, 41 such as a portable device, possibly after a notification of a newly published data set, a care area, a drug library or a configuration. Once, the user 6 has downloaded the data to the communication device 40, 41, the user 6 transfers the data to the rack 31 using a sequence as shown in FIG. 5. Herein, first the user 6 scans the barcode 8 attached to or displayed on the infusion device 32 to which the data shall be transferred or the rack 31 to which the infusion device 32 is attached (step S1). Upon scanning of the barcode 8 the user 6 is directed to the web server 310 of the rack 31 (step S2) and, by means of the web server 310, transfers the data to the rack 31 (step S3). Once the data is transferred to the rack 31 via the web server 310 (step S4), the user 6 may initiate a distribution of the data to one or multiple infusion devices 32 attached to the rack 31 by inputting a respective command via the web server 310, which then informs the rack 31 accordingly (steps S5, S6 and S7).

By using this sequence it can be made sure that operational data is not transferred to infusion pumps 32 while the infusion pumps 32 are in the process of infusing drugs to patients. For this, the user 6 first downloads the data to be installed to his communication device 40, 41 and then transfers the data, via the rack 31, to the respective infusion devices 32.

The idea of the invention is not limited to the embodiments described above.

By means of a web-based service provided via a drug library server of the kind described above located in the public domain, for example on the internet, it becomes possible to easily distribute and share operational data within a particular healthcare environment, for example a hospital, and even a across separate healthcare environments, for example different hospitals.

By outputting operational data in a standardized format, such as an XML or JSON/BSON format, the web based service may function with medical devices of different manufacturers.

The data may for example be parameterized using existing definitions of parameterizing drugs, as for example known from the so called HL7/IHE representations and the HIBC barcoding standard for smart pumps/IV medication.

LIST OF REFERENCE NUMERALS

1 Drug library server
10 Web server
11 Communication interface (web interface components)
12 Database components
120 Device localization
121 Client profiles
122 Configurations
123 Drug libraries
124 Care areas
125 Data sets
126 Device profiles,
13 Manufacturer tools
2 Public communication network
3 Healthcare environment
30 Interface
31 Medical device (rack)
310 Communication interface (web server)
32 Medical device (infusion pump)
320 Communication interface (web server)
33 Local network
34 Distribution server
340 Communication interface (web server)

40 Communication device (portable device)
400 Web client
41 Communication device (external device)
410 Web client
411 Device discovery tool
5 External services
50 External systems
51 Manufacturer services
6 User
8 Barcode
81 Information
S1-S7 Steps

The invention claimed is:

1. A method for transferring operational data to a medical device for administering a drug to a patient, the medical device being located in a healthcare environment and connected to a non-public, private local network, the method comprising the steps of:
   providing operational data to be transferred to the medical device on a drug library server located within a public communication network, the operational data relating to drug library data defining at least one of rules for compatibility and rules for administration associated with a drug, wherein the drug library server is not able to communicate with medical devices connected to the non-public, private local network and cannot obtain information on medical devices connected to the non-public, private local network,
   transferring said operational data to be transferred to the medical device from the drug library server to a hand-held portable communication device via the public communication network,
   reading, by means of the communication device, information from an identification tag attached to or displayed on the medical device, wherein the information causes the communication device to access a communication interface constituted by a web server associated with the medical device,
   establishing a web link to the communication interface on the medical device for a direct transfer of the operational data from the communication device to the medical device upon reading the information from the identification tag attached to or displayed on the medical device, and
   transferring the operational data from the communication device via the communication interface to the medical device over a wireless connection,
   wherein the web server comprises a backend that is configured to handle the received operational data for installation on the medical device and to check integrity, validity, and persistency of the operational data.

2. The method according to claim 1, wherein the communication interface provides operational information about the medical device.

3. The method according to claim 1, wherein the medical device is an infusion device for administering a drug to a patient or a rack constituted to be connected to at least one infusion pump.

4. The method according to claim 1, wherein the identification tag is a barcode.

5. The method according to claim 1, wherein the identification tag is static or dynamic.

6. The method according to claim 1, wherein the public communication network is the internet.

7. The method according to claim 1, wherein the communication device comprises a web client for communicating with the drug library server via the public communication network.

8. The method according to claim 1, wherein the drug library server is constituted to output operational data in a flat file format or an XML or JSON/BSON format.

9. The method according to claim 1, wherein the healthcare environment comprises a plurality of wards in a hospital.

10. The method according to claim 1, wherein the healthcare environment comprises a plurality of hospitals.

11. A method for transferring operational data to a medical device for administering a drug to a patient, the medical device being located in a healthcare environment and connected to a non-public, private local network, the method comprising the steps of:
    providing operational data to be transferred to the medical device on a drug library server located within a public communication network, the operational data relating to drug library data defining at least one of rules for compatibility and rules for administration associated with a drug, wherein the drug library server is not able to communicate with medical devices connected to the non-public, private local network and cannot obtain information on medical devices connected to the non-public, private local network,
    transferring said operational data to be transferred to the medical device from the drug library server to a hand-held portable communication device via the public communication network,
    reading, by means of the communication device, information from an identification tag attached to or displayed on the medical device, wherein the information causes the communication device to access a communication interface constituted by a web server associated with the medical device,
    establishing a web link to the communication interface on the medical device for a direct transfer of the operational data from the communication device to the medical device upon reading the information from the identification tag attached to or displayed on the medical device, and
    transferring the operational data from the communication device via the communication interface to the medical device over a wireless connection,
    wherein the information from the identification tag comprises an IP or hostname address or HTTP address of a web page on the web server.

12. A method for transferring operational data to a medical device for administering a drug to a patient, the medical device being located in a healthcare environment and connected to a non-public, private local network, the method comprising the steps of:
    providing operational data to be transferred to the medical device on a drug library server located within a public communication network, the operational data relating to drug library data defining at least one of rules for compatibility and rules for administration associated with a drug, wherein the drug library server is not able to communicate with medical devices connected to the non-public, private local network and cannot obtain information on medical devices connected to the non-public, private local network, transferring said operational data to be transferred to the medical device from the drug library server to a hand-held portable communication device via the public communication network, reading, by means of the communication device, information from an identification tag attached to or displayed on the medical device, wherein the information causes the communication device to access a communication interface constituted by a web server associated with the medical device, establishing a web link to the communication interface on the medical device for a direct transfer of the operational data from the communication device to the medical device upon reading the information from the identification tag attached to or displayed on the medical device, and transferring the operational data from the communication device via the communication interface to the medical device over a wireless connection, wherein establishing the web link to the communication interface comprises the communication device accessing a web page provided by the web server implemented on the medical device, the web page containing a file upload object.

13. The method according to claim 12, wherein transferring the operational data comprises, automatically or by user interaction, selecting a file to upload and transferring the file to the medical device after the communication device accesses the web page.

14. The method according to claim 1, wherein the hand-held portable communication device comprises at least one of a mobile phone, a personal digital assistant, and a tablet computer.

15. The method according to claim 11, wherein the hand-held portable communication device comprises at least one of a mobile phone, a personal digital assistant, and a tablet computer.

16. The method according to claim 12, wherein the hand-held portable communication device comprises at least one of a mobile phone, a personal digital assistant, and a tablet computer.

* * * * *